United States Patent [19]

Meltsner et al.

[11] 4,308,407
[45] Dec. 29, 1981

[54] CHEMICAL PROCESS

[75] Inventors: Bernard R. Meltsner, Royal Oak; Joseph D. Odenweller, Bloomfield Hills, both of Mich.

[73] Assignee: Ethyl Corporation, Richmond, Va.

[21] Appl. No.: 179,051

[22] Filed: Aug. 18, 1980

[51] Int. Cl.$^3$ ............................................. C07C 39/06
[52] U.S. Cl. ..................................... 568/784; 568/774
[58] Field of Search ........................ 568/780, 784, 774

[56] References Cited

U.S. PATENT DOCUMENTS

| | | | |
|---|---|---|---|
| 2,576,161 | 11/1951 | Thompson | 568/784 |
| 2,725,402 | 11/1955 | Britton et al. | 568/774 |
| 2,803,669 | 8/1957 | Brainerd et al. | 568/774 |
| 2,841,624 | 7/1958 | Norton et al. | |
| 3,006,969 | 10/1961 | Koetiz | |
| 3,030,428 | 4/1962 | Morris et al. | |
| 4,072,724 | 2/1978 | Parker | 568/784 |
| 4,117,244 | 9/1978 | Abramov et al. | |
| 4,228,308 | 10/1980 | MacLaury | 568/774 |

*Primary Examiner*—Werren B. Lone
*Attorney, Agent, or Firm*—Donald L. Johnson; Joseph D. Odenweller; John F. Hunt

[57] ABSTRACT

Phenols with a methyl group substituted on the phenolic benzene ring, such as 2,6-di-tert-butyl-p-cresol, can be produced by reacting a halomethyl group substituted on a phenol such as 2,6-di-tert-butyl-4-chloromethyl-phenol, with hydrogen in the presence of a hydrogenation catalyst, such as palladium.

13 Claims, No Drawings

CHEMICAL PROCESS

BACKGROUND OF THE INVENTION 2,6-Di-tert-butyl-4-methylphenol is a known antioxidant. Various methods are available for its production.

U.S. Pat. No. 2,841,624 describes a process whereby 2,6-di-tert-butyl-4-methylphenol can be produced by reacting 3,5-di-tert-butyl-4-hydroxybenzyl alcohol or ether in the presence of an alcohol and a base.

U.S. Pat. No. 3,006,969 teaches the catalytic hydrogenation of 3,5-di-tert-butyl-4-hydroxybenzyl methyl ether to obtain 2,6-di-tert-butyl-4-methylphenol.

U.S. Pat. No. 3,030,428 indicates that 2,6-di-tert-butyl-4-methylphenol can be made by reacting 3,5-di-tert-butyl-4-hydroxybenzyl alcohol with hydrogen in the presence of a catalyst.

U.S. Pat. No. 4,117,244 teaches the production of 2,6-di-tert-butyl-4-methylphenol by the catalytic hydrogenation of N,N-dimethyl-3,5-di-tert-butyl-4-hydroxybenzyl amine.

A halomethyl group substituted on an aromatic compound may be converted to a methyl group by a variety of known chemical reducing agents. The article "9-BBN Ate Complexes As A New Type Of Reducing Agent For The Selective Reduction Of Tertiary Alkyl, Benzyl, And Allyl Halides To Hydrocarbons" in *J. Am. Chem. Soc.*, (1975) 97:9, pages 2558-9, discusses the selective removal of a number of types of halides to afford the corresponding hydrocarbons in excellent yields without concomitant attack on secondary, primary and aryl derivatives. Several substrates were reduced including benzyl chloride to toluene and diphenylchloromethane to diphenylmethane.

"Organic Reactions," Volume VII, Chapter 5, pages 263 through 326 discusses the hydrogenolysis of benzyl groups attached to oxygen, nitrogen and sulfur using a palladium catalyst to obtain a methyl group substituted on an aromatic ring. The technique whereby a halomethyl group attached to an aromatic ring is converted to a methyl group is not considered.

SUMMARY OF THE INVENTION

In accordance with the present invention, a cresol can be produced by reacting a halomethylphenol with hydrogen in the presence of a hydrogenation catalyst.

DESCRIPTION OF THE PREFERRED EMBODIMENTS

A preferred embodiment for this invention is a process for converting a halomethylphenol to a cresol, said process comprising reacting said halomethylphenol with hydrogen in the presence of a hydrogenation catalyst.

The halomethylphenols are exemplified by p-chloromethylphenol, 3-methyl-5-bromomethylphenol, 2-chloromethyl-5-tert-butylphenol, phenyl-2-hydroxy-4-chloromethylbenzoate, 2-hydroxy-5-bromomethylphenyl methyl ketone, 2-chloromethyl-3-hydroxy benzoic acid, 1-bromomethyl-3-hydroxy naphthalene, 2-hydroxy-4-chloromethyldiphenyl and 2-chloro-4-hydroxy benzyl chloride.

A more preferred embodiment of the invention involves reacting a dihydrocarbyl chloromethylphenol having the structure:

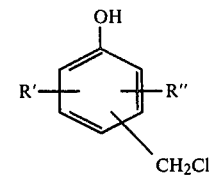

wherein R' and R" are selected from the group consisting of alkyl containing 1 to 20 carbon atoms, cycloalkyl containing 5 to 8 carbon atoms, aralkyl containing 7 to 20 carbon atoms and aryl containing 6 to 20 carbon atoms with hydrogen in the presence of a hydrogenation catalyst.

The dihydrocarbyl chloromethyl phenolic compounds containing R' and R" are exemplified by 2-methyl-4-chloromethyl-6-ethylphenol, 3-decyl-4-pentyl-5-chloromethylphenol, 2-chloromethyl-4,6-dipentadecylphenol, 2-propyl-4-chloromethyl-6-eicosylphenol, 3-cyclohexyl-4-chloromethyl-5-cyclopentylphenol, 2-cyclooctyl-4-cycloheptyl-6-chloromethylphenol, 2-cyclopentyl-4-chloromethyl-6-cyclopentylphenol, 2,6-di-(α-methylbenzyl)-4-chloromethylphenol, 2,6-di-(α,α-dimethylbenzyl)-4-chloromethylphenol, 2-(4-sec-dodecyl-α-methylbenzyl)-4-chloromethyl-6-methylphenol and the like.

An even more preferred embodiment for this invention involves reacting a 2,6-di-alkyl-4-chloromethylphenol with hydrogen in the presence of a hydrogenation catalyst. These compounds are exemplified by 2-tert-butyl-4-chloromethyl-6-methylphenol, 2-sec-hexyl-4-chloromethyl-6-sec-decylphenol and 2-methyl-4-chloromethyl-6-sec-eicosylphenol.

The most preferred embodiment of the invention involves the catalytic hydrogenation of 2,6-di-tert-butyl-4-chloromethylphenol.

The preferred catalysts for this conversion include the well-known group of hydrogenation catalysts which are selected from the group consisting of Group VIII metals, chromium and molybdenum and compounds thereof. These can be exemplified by copper chromite, Raney nickel, platinum, rhodium and the like.

More preferred catalysts include those of the platinum group of metals, such as platinum, palladium, ruthenium and rhodium. The most preferred catalyst is palladium.

The amount of catalyst used can vary over a wide range. It depends on the type of catalyst and the reaction conditions. A useful range is about 0.001–0.1 moles of catalyst per mole of hydroxybenzyl halide.

The preferred reaction conditions include a hydrogen pressure high enough to allow the reaction to proceed at a reasonable rate yet not so high as to adversely affect the course of the reaction. The preferred pressure range extends from atmospheric to about 3,000 psig. A more preferred pressure range is from 50 to 2,000 psig. An even more preferred pressure range is from 100 to 1,000 psig. The most preferred pressure range is from 300 to 600 psig.

The reaction is conducted at a temperature high enough to cause the reaction to proceed, yet not so high as to adversely affect the course of the reaction. The preferred temperature range is from about 25° C. to 300° C. A more preferred temperature range extends from 30° C. to 200° C. An even more preferred temperature range is from 50° C. to 150° C. The most preferred temperature range is from 60° C. to 80° C.

Solvents are not essential since many of the halomethyl compounds are liquids; however, it is preferred to conduct the process in a solvent. The solvent can be selected from aliphatic hydrocarbons, aromatic hydrocarbons or halogenated hydrocarbons. Examples of aliphatic hydrocarbons include pentane, hexane, heptane, petroleum ether and the lile. Examples of halogenated hydrocarbons include dichloromethane, trichloroethane, chlorobenzene, dichlorobenzene and the like. Solvents can also be selected from alcohols, such as tert-butanol and isopropanol, or ethers, such as tetrahydrafuran, the dimethyl ether of ethylene glycol, or glycol ethers, such as the monoethyl ether of diethylene glycol or the methyl ether of ethylene glycol.

The following example illustrates the way the process is conducted.

EXAMPLE

To a 50 ml glass liner in a 300 ml rocking autoclave was added 30 grams of a toluene solution containing 46% 2,6-di-tert-butyl-4-chloromethylphenol. To this was added 0.5 gram of 5% palladium on activated charcoal. The autoclave was closed and pressurized with hydrogen. The reaction mixture was held for two hours at 70° C. The pressure within the autoclave dropped from an initial 600 psig to 550 psig during the course of the reaction. The autoclave was then cooled and vented. The reaction mixture was filtered to remove the catalyst. The resultant solution was clear and lacked the yellow color of the starting material. The reaction mixture was analyzed by Vapor Phase Chromatography. The results were 48% toluene, 37.9% 2,6-di-tert-butyl-p-cresol, 3.4% 4,4'-methylenebis-(2,6-di-tert-butylphenol) and miscellaneous phenolic impurities.

The invention is not limited to the foregoing description. A wide variety of starting materials may be used. For instance, 4-bromomethyl-2-tert-butyl-6-methylphenol can be substituted for 2,6-di-tert-butyl-4-chloromethylphenol to obtain 2-tert-butyl-4,6-dimethylphenol via the above catalytic hydrogenation. 4-Chloromethyl-2,6-dicyclopentylphenol is converted to 4-methyl-2,6-dicyclopentylphenol. Likewise, 5-bromomethyl-3-decyl-4-pentylphenol is converted to 3-decyl-5-methyl-4-pentylphenol.

We claim:

1. A process for converting a halomethyl phenol to a cresol, said process comprising contacting said halomethyl phenol with hydrogen in the presence of a hydrogenation catalyst at a pressure of from atmospheric to about 3000 psig and at a temperature of from about 25° C. to about 300° C.

2. A process of claim 1 wherein said halomethyl phenol is a chloromethyl phenol.

3. A process of claim 2 wherein said hydrogenation catalyst is selected from the group consisting of Group VIII metals, chromium and molybdenum and compounds thereof.

4. A process of claim 3 wherein said hydrogenation catalyst is palladium.

5. A process of claim 1 for making a dihydrocarbyl cresol by contacting a dihydrocarbyl chloromethyl phenol having the structure:

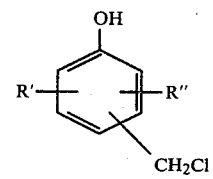

wherein R' and R" are selected from the group consisting of alkyl containing 1 to 20 carbon atoms, cycloalkyl containing 5 to 8 carbon atoms, aralkyl containing 7 to 20 carbon atoms and aryl containing 6 to 20 carbon atoms, with hydrogen in the presence of a hydrogenation catalyst at a pressure of from atmospheric to about 3000 psig and at a temperature of from about 25° C. to about 300° C.

6. A process of claim 5 wherein said hydrogenation catalyst is selected from the group consisting of Group VIII metals, chromium and molybdenum and compounds thereof.

7. A process of claim 6 wherein said hydrogenation catalyst is palladium.

8. A process of claim 5 wherein said dihydrocarbyl chloromethyl phenol is a 2,6-di-alkyl-4-chloromethyl phenol.

9. A process of claim 8 wherein said hydrogenation catalyst is selected from the group consisting of Group VIII metals, chromium and molybdenum and compounds thereof.

10. A process of claim 9 wherein said hydrogenation catalyst is palladium.

11. A process of claim 8 wherein said 2,6-di-alkyl-4-chloromethyl phenol is 2,6-di-tert-butyl-4-chloromethyl phenol.

12. A process of claim 11 wherein said hydrogenation catalyst is selected from the group consisting of Group VIII metals, chromium and molybdenum and compounds thereof.

13. A process of claim 12 wherein said hydrogenation catalyst is palladium.

* * * * *